United States Patent
Laghi et al.

(10) Patent No.: US 11,224,526 B2
(45) Date of Patent: Jan. 18, 2022

(54) PROSTHETIC LINER WITH EXTERNAL FABRIC SEAL

(71) Applicants: Alps South Europe S.R.O., Plzen (CZ); Aldo Laghi, Pinellas Park, FL (US)

(72) Inventors: Aldo Laghi, Pinellas Park, FL (US); Nathaniel Vint, Oldsmar, FL (US)

(*) Notice: Subject to any disclaimer, the term of this patent is extended or adjusted under 35 U.S.C. 154(b) by 0 days.

(21) Appl. No.: 16/258,621

(22) Filed: Jan. 27, 2019

(65) Prior Publication Data
US 2020/0069443 A1  Mar. 5, 2020

Related U.S. Application Data

(63) Continuation-in-part of application No. 16/120,791, filed on Sep. 4, 2018.

(51) Int. Cl.
| A61F 2/78 | (2006.01) |
| A61F 2/80 | (2006.01) |
| A61F 2/50 | (2006.01) |

(52) U.S. Cl.
CPC .............. *A61F 2/80* (2013.01); *A61F 2/7812* (2013.01); *A61F 2002/5007* (2013.01); *A61F 2002/7818* (2013.01); *A61F 2002/7837* (2013.01); *A61F 2002/802* (2013.01)

(58) Field of Classification Search
CPC .. A61F 2/7812; A61F 2/80; A61F 2002/5007; A61F 2002/7818; A61F 2002/7837; A61F 2002/802; A61F 2002/785
See application file for complete search history.

(56) References Cited

U.S. PATENT DOCUMENTS

| 5,314,497 | A  | * | 5/1994  | Fay .................. | A61F 2/7843 623/33 |
| 6,136,039 | A  | * | 10/2000 | Kristinsson ........ | A61F 2/7812 623/36 |
| 7,169,189 | B2 | * | 1/2007  | Bjarnason ........... | A61F 2/7812 602/26 |
| 8,097,043 | B2 |   | 1/2012  | Egilsson           |                 |
| 8,123,818 | B2 | * | 2/2012  | Bjarnason ........... | A61F 2/7812 623/36 |

(Continued)

FOREIGN PATENT DOCUMENTS

DE  102017108913 A1  10/2018

*Primary Examiner* — Jerrah Edwards
*Assistant Examiner* — Melissa A Hoban
(74) *Attorney, Agent, or Firm* — GrayRobinson, P.A.

(57) ABSTRACT

A prosthetic liner for use with a prosthetic socket that has a thermoplastic elastomeric (TPE) layer that is in contact with the amputee's residual limb. The TPE layer is not uniform in thickness but has ridges to extend circumferentially around the TPE layer. A fabric exterior layer covers the outer surface of the TPE layer conforming to the ridges and is used as a substrate to form a mechanical bond to an elastomeric material. Impregnating the elastomeric material within the fabric exterior occurs by applying an uncured material to the fabric exterior layer and onto at least the apex surfaces located within the sealing regions thereby creating an air tight boundary layer when inserted into a socket. When a vacuum is applied the air is evacuated from the volume below the seal layer.

22 Claims, 15 Drawing Sheets

(56) References Cited

U.S. PATENT DOCUMENTS

| | | | |
|---|---|---|---|
| 8,828,094 B2* | 9/2014 | Halldorsson | A61F 2/80 623/36 |
| 8,894,719 B2* | 11/2014 | Egilsson | A61F 2/80 623/36 |
| 8,956,422 B2* | 2/2015 | Halldorsson | A61F 2/7812 623/36 |
| 10,322,016 B2* | 6/2019 | Birgisdottir | A61F 2/80 |
| 10,420,657 B2* | 9/2019 | Jonsson | A61F 2/80 |
| 2009/0132056 A1 | 5/2009 | Kania | |
| 2012/0116538 A1 | 5/2012 | Patterson | |
| 2015/0142132 A1* | 5/2015 | Egilsson | A61F 2/80 623/35 |
| 2016/0022441 A1 | 1/2016 | Rowe | |
| 2017/0304085 A1 | 10/2017 | Kurth | |
| 2020/0069443 A1* | 3/2020 | Laghi | A61F 2/80 |

* cited by examiner

PROSTHETIC LINER WITH EXTERNAL FABRIC SEAL

CROSS-REFERENCE TO RELATED APPLICATIONS

This application is a continuation-in-part of application Ser. No. 16/120,791, filed Sep. 4, 2018, entitled "Prosthetic Liner with External Fabric Seal," the contents of which are hereby incorporated by reference herein.

BACKGROUND OF THE INVENTION

Field of the Invention

This invention relates to liners for use in a prosthetic assembly. More particularly, this invention relates to vacuum sealing liners having a thermoplastic elastomeric layer comprising sealing ridges such that an air tight seal is formed when a vacuum is applied within the area between a prosthetic socket and the sealing liner.

Description of the Background Art

Presently, suspension liners can be configured to provide a sealing means between a residual limb and a prosthetic socket as seen in U.S. Pat. No. 8,097,043 to Egilsson, the disclosure of which is hereby incorporated by reference herein. Such liner sleeves are typically made of an air impermeable elastomer material such as silicone and may include a reinforcement layer intermediate the inner and outer surfaces of the liner sleeve body portion or externally thereof to provide resistance against axial elongation of the elastomer constituting the liner sleeve body. Such reinforcement typically does not restrict radial distension or stretching of the liner sleeve body.

Various arrangements have been considered when configuring the suspension liners to securely remain within the rigid prosthetic socket because the ambulation of the user typically wiggles the prosthetic away from the user's residual limb. Of the various method, such as ambulation-pumping mechanisms to remove any remaining air from the space between the liner to the prosthetic, a most efficient method is to prepare a seal around the liner. This seal suspension liner has an elastomeric material attached to the knitted layer to provide a friction-inducing property to the liner itself. When the user inserts her residual limb, with attached suspension liner, the user would in effect, force her limb into the prosthetic socket and then the ring-like seal, which has a larger circumference than the suspension liner, being jammed into the prosthetic.

In other applications, it may be desired to more positively secure the liner sleeve within the socket by creating a hypobaric (vacuum) pressure within the distal end of the hard socket and the distal end of a suspension liner sleeve inserted into the socket. The hypobaric pressure may be maintained at the distal end of the hard socket and the interior of the socket at its distal end will be isolated from atmosphere during normal retention of the sleeve liner within the socket. Opening the distal end of the socket to atmosphere releases the vacuum or hypobaric pressure within the socket to enable simple withdrawal of a residual limb with a liner sleeve thereon from the socket. A pump or other device may be utilized to evacuate the distal end of the socket between the distal end of a liner sleeve and the distal end of a socket. A valve or other appropriate device typically is used to open and close the distal end of a socket to surrounding atmosphere.

Other arrangements are known in the prior art for providing an appropriate seal between the exterior of the liner sleeve and the interior of the hard socket including external air impermeable sleeves covering the interface area between the proximal end of the hard socket and the adjacent liner sleeve body.

Therefore, it is an object of this invention to provide an improvement which overcomes the aforementioned inadequacies of the prior art devices and provides an improvement which is a significant contribution to the advancement of the liner art.

Another objective of the invention is to create a convenient, improved sealing arrangement between an elastomeric liner sleeve and the interior of a prosthetic socket.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The present invention relates generally to a layered liner with ridges for use in a prosthetic assembly. Specifically, the present invention relates to a liner having an elastomer layer, a fabric exterior, and a sealing layer wherein the elastomer layer has a plurality of ridges. The fabric exterior is bonded to the outer surface of the elastomer layer and forms a suitable substrate for having an elastomeric material impregnated within. The sealing layer is applied in an uncured state to the fabric with a purpose of having a viscosity such that the sealing layer is able to "wet out" the fabric in the applied area so that once cured, the sealing layer forms an air tight seal intermediate the fabric and socket.

Typically, the sealing ridges are formed by a separate molding process than that of the elastomeric layer. That is, the elastomeric layer does not have any sealing ridges because the sealing ridges are essentially, implanted via bonding agents to the knitted layer or elastomeric layer. In this situation, when the sealing ridges are implanted into the elastomeric layer, they are called raised portions. However, in this invention, having the elastomeric layer configured to be molded to include the plurality of sealing ridges offers an advantage over similar technology. The raised portions are more durable because they are protected by not only the reinforcement layer, but also the outer layer that covers only the sealing ridges. Thus, if the outer layer is eventually removed via continuous use over many years, the suspension liner will still have a slight sealing effect because the raised portions are still within the elastomeric layer.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which.

Similar reference numerals refer to similar parts throughout the several views of the drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
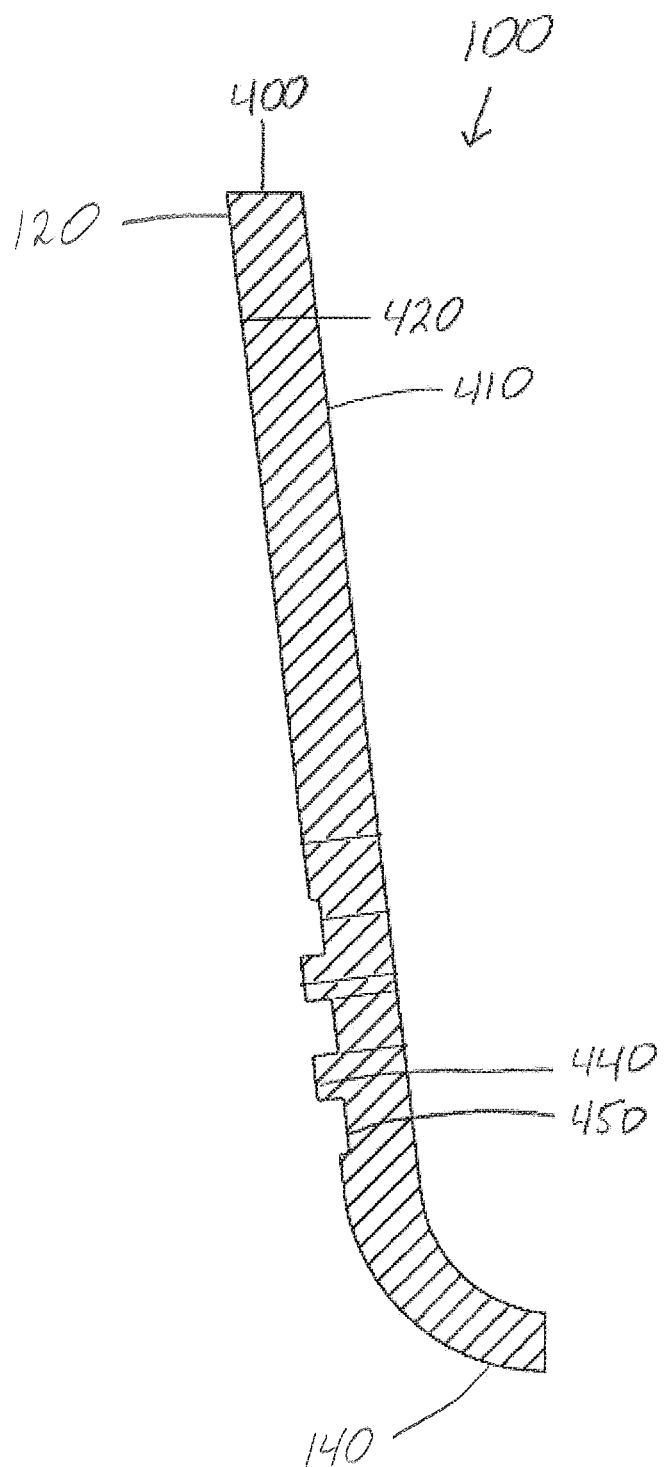
FIG. 1 is a cross-sectional view of the thermoplastic elastomeric layer.

FIG. 1 illustrates a thermoplastic elastomeric layer 400 of the seal liner 100 in which the thermoplastic elastomer layer 400 (also known as TPE) having an inner elastomer surface 410 and outer elastomer surface 420 is formed within a mold having wall thicknesses between 2 and 9 mm. The liner 100 preferable has an open proximal end 120 with a larger circumference and volume than of the closed distal end 140.

Figure 2:
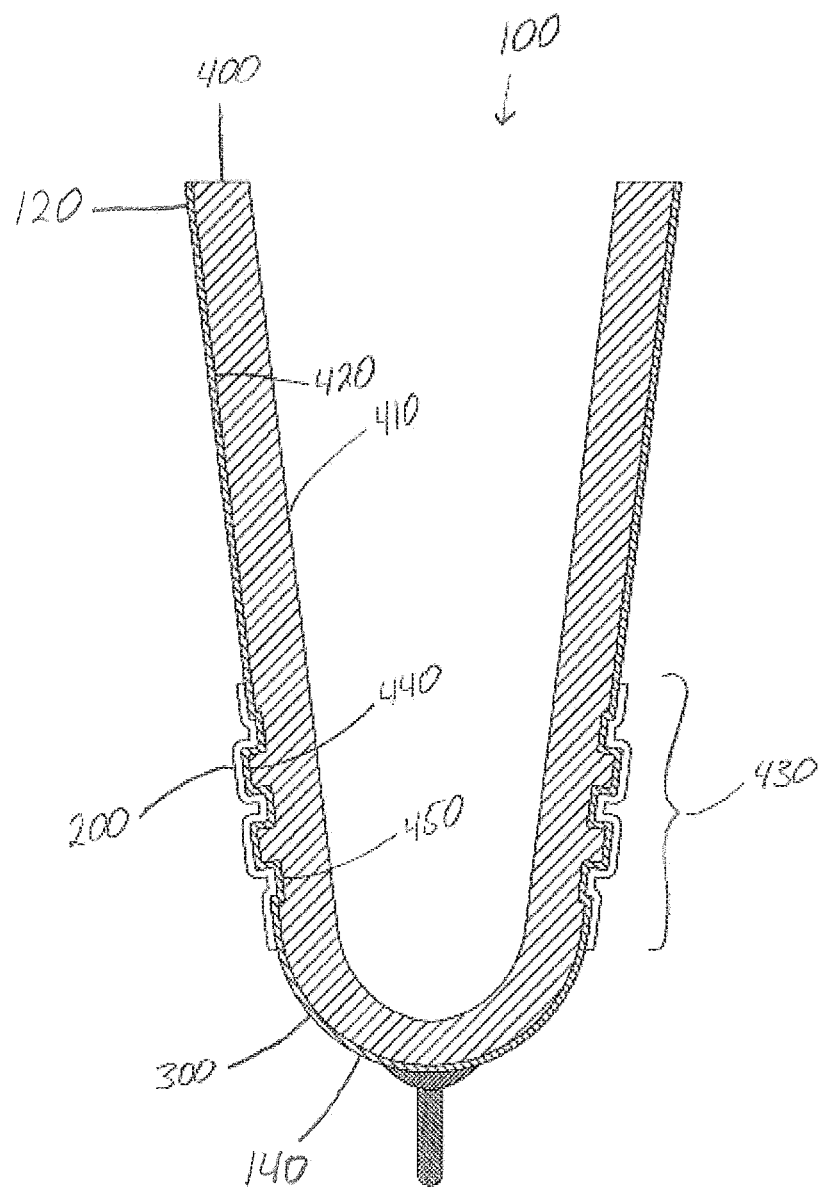
FIG. 2 is a cross-sectional view of the preferred embodiment of the suspension sleeve liner.
Figure 3:
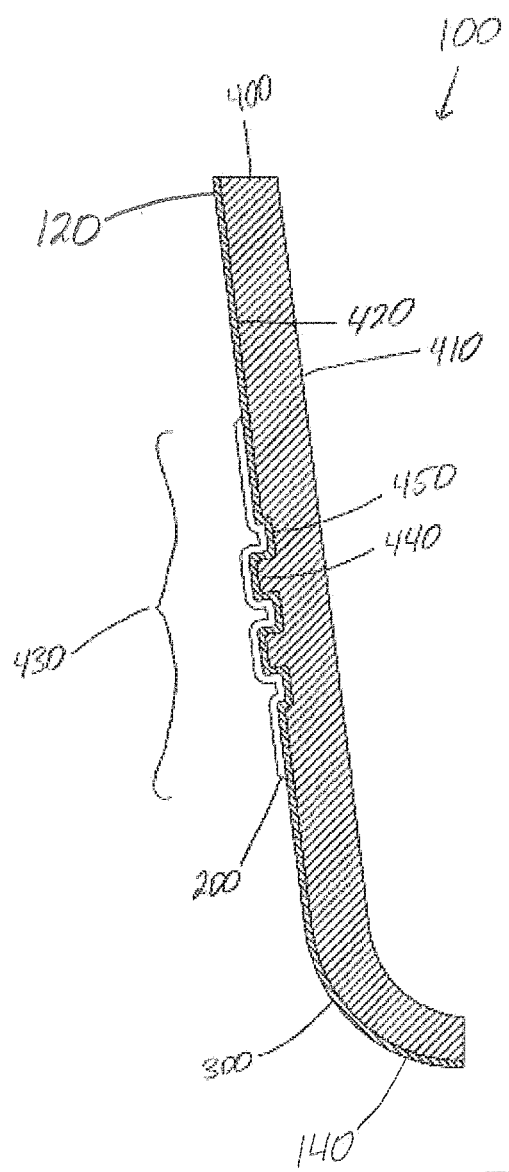
FIGS. 3-11 are cross-sectional views of suspension sleeve liners corresponding to FIG. 2 wherein alternate embodiments of the raised and recessed portions are shown.
Figure 4:
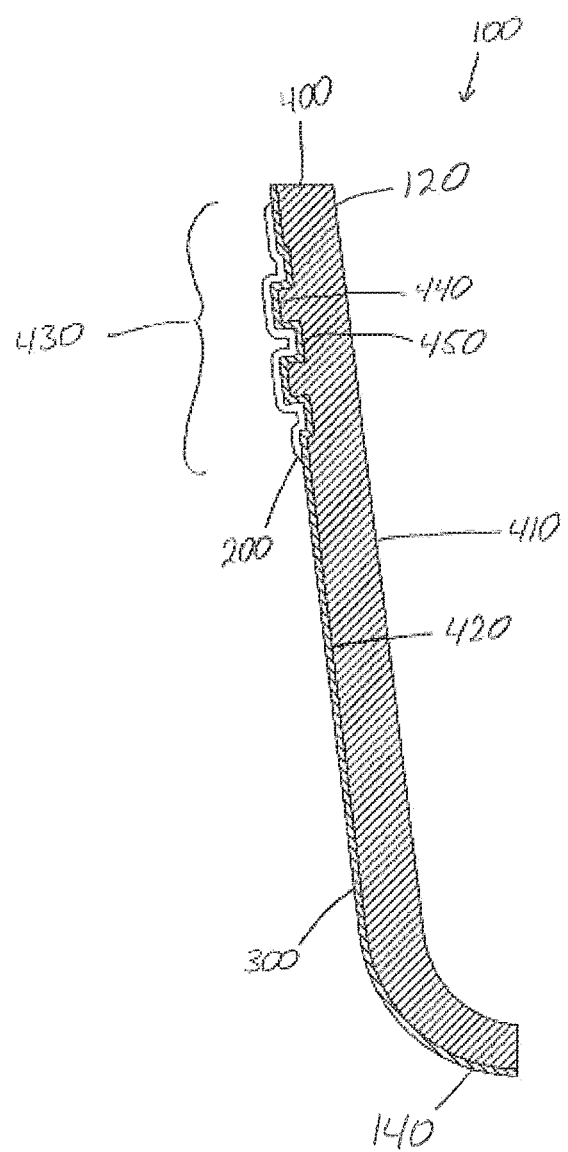
Figure 5:
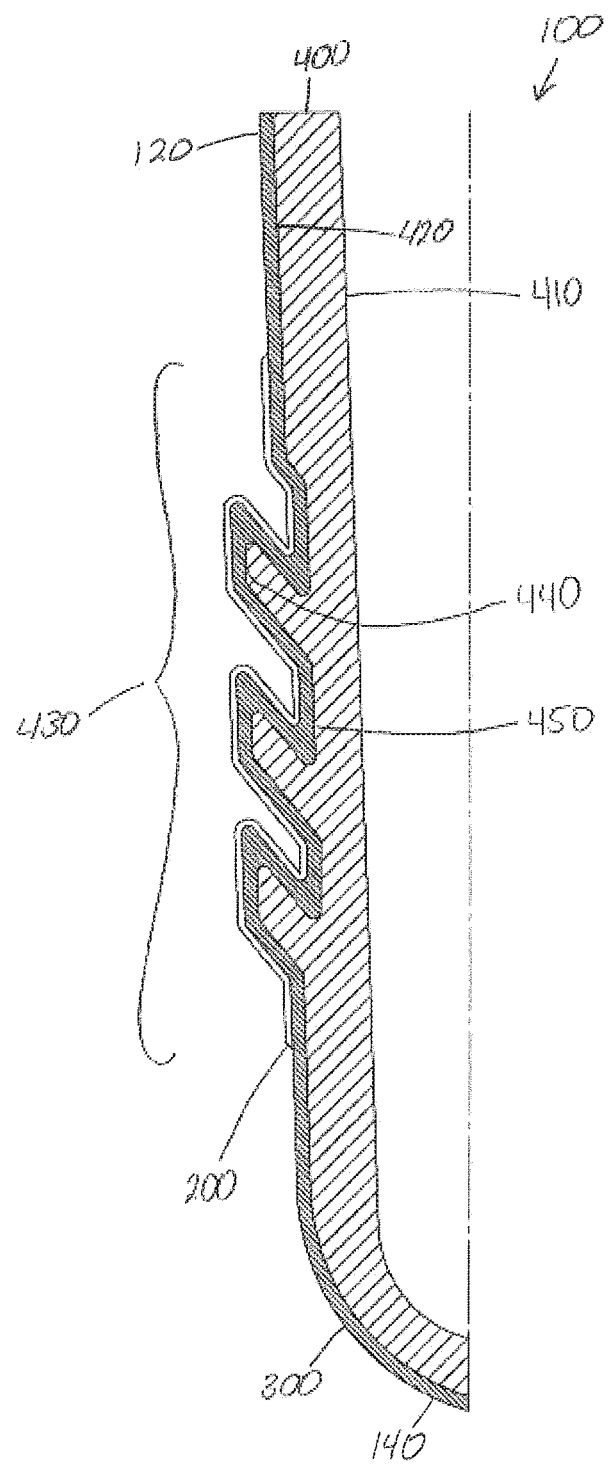
Figure 6:
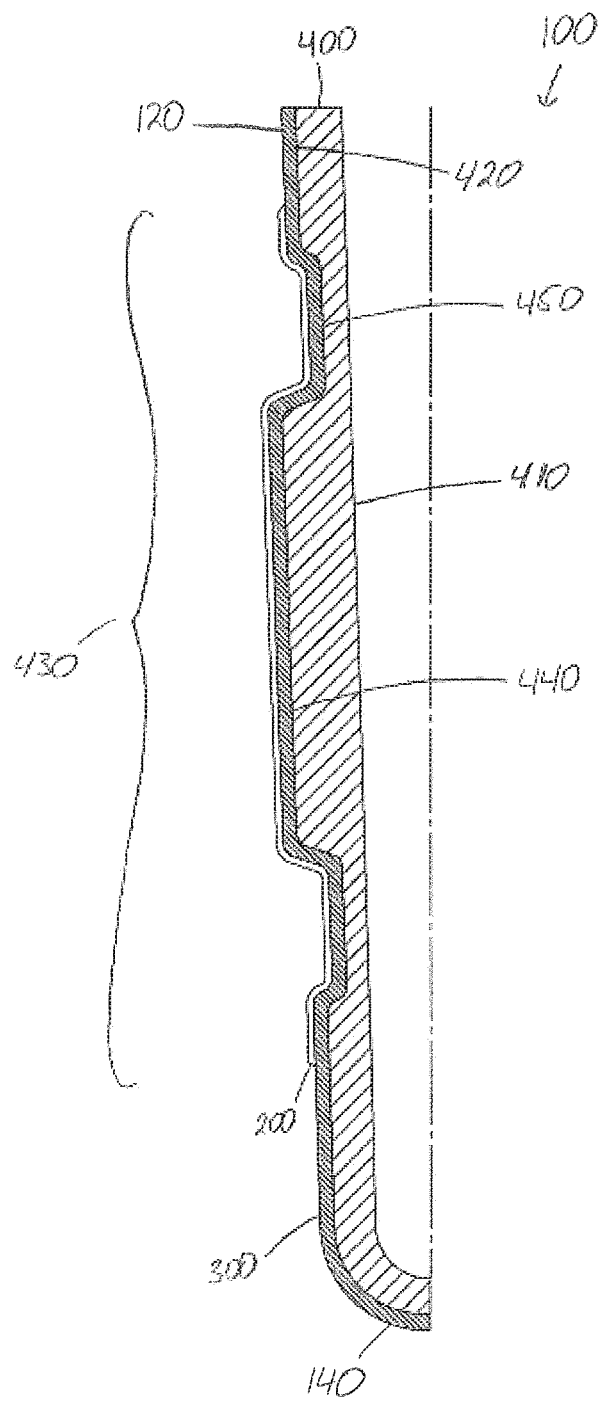
Figure 7:
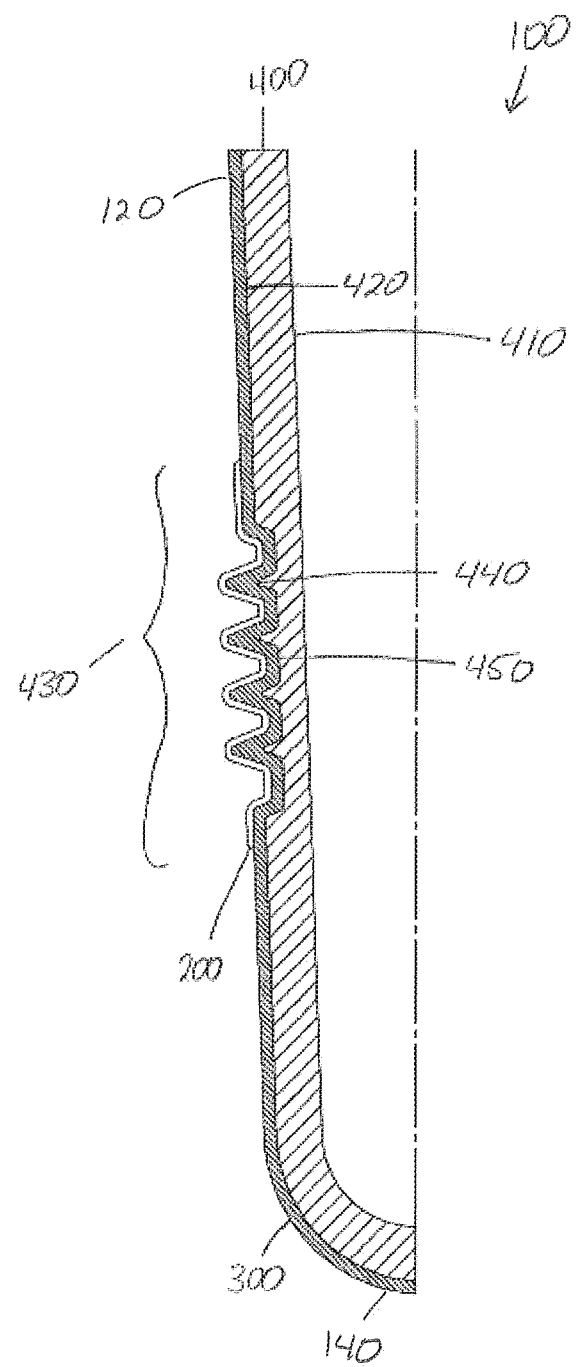

FIG. 2 illustrates a preferred embodiment of the seal liner 100 in which the thermoplastic elastomer layer 400 further comprises at least one sealing region 430 that extends preferably between 3 and 20 mm outward from the interior surface 410 of the thermoplastic elastomeric layer 400 and includes at least one raised portion 440. If more than one raised portion 440 is included within the sealing region 430, the plurality of raised portions 440 will be accompanied by at least one recessed portion 450. Thus, if there are two raised portions 440 then three recessed portions 450 will be distributed as shown in FIG. 1. Alternatively, the sealing region 430 may begin with a raised portion 440 instead of a recessed portion 450. In this instance, the distribution would be as follows: raised portion 440, recessed portion 450, raised portion 440. Thus, the recessed portions 450 do not always have to surround distal and proximal ends of the sealing region 430.

A fabric exterior 300 is synonymous with "reinforcement layer" and is bonded to the outer elastomer surface 420 of the thermoplastic elastomer layer 400 and conforms to the at least one sealing region 430. The fabric exterior 300 advantageously forms a suitable substrate for bonding a seal layer 200. The seal layer 200 conforms to the shape of the fabric exterior 300 and thermoplastic elastomer layer 400. The seal layer 200 is applied in an uncured state to the fabric and with a viscosity such that it is able to "wet out" the fabric in that area so that once cured it forms an air tight seal thus isolating the fabric above the seal layer (not shown) from the fabric exterior 300 below the seal layer 200. Thus, this application of the outer sealing layer 200 to the fabric exterior 300 provides an air-impermeable interface between the thermoplastic elastomeric layer 400 and the surrounding exterior area of the liner 100. The outer sealing layer 200 is preferably applied such that it impregnates the reinforcement layer 300 so as to form a composite.

This outer sealing layer 200 may be comprised of natural rubber, silicone, polyurethane, latex, polysulfide, vinyl, polyisoprene, or a styrene block copolymer gel, although the preferred material is rubber due to their high abrasion resistance and high force to stretch. The force to stretch this layer is determined by the modulus of elasticity of the sealing material multiplied by the cross-sectional area of the sealing material.

The thermoplastic elastomer layer 400 is preferably of a type compatible with long periods of dynamic wearer contact. Such materials are known in the art and may include the following polymers, as well as gels which comprise them: silicones polyurethanes; block copolymers such as styrene block copolymer gels, general non-limiting examples of which may include SEBS-, SEPS-, SEEPS-, SEEBS-, and other type styrene block copolymer gels. Further non-limiting examples of styrene block copolymer gels which may be useful in the liner of the present invention include so called "controlled distribution polymers," such as, for example, those disclosed in U.S. Pat. No. 7,226,484; United States Patent Application Publication No. 20070238835; and United States Patent Application Publication No. 20050008669, the disclosure of which is hereby incorporated by reference herein. Other potentially useful polymers may include certain so-called "crystalline" polymers, such as, for example, polymers disclosed in U.S. Pat. Nos. 5,952,396; 6,420,475 and 6,148,830, the disclosures of which are hereby incorporated by reference herein. The above list is non-limiting, and in general, the list of acceptable polymers and gels includes those known in the art to be useful for the fabrication of prosthetic liners. The term "gel" is defined to be a polymer mixed with a plasticizer. An example of current liner using such gel is the "EZ Gel"™ liner, available from Alps South, LLC.

The term "sealing region" 430 may include only one raised portion 440 or may include a plurality. If it includes a plurality of raised portions 440, the sealing region 430 will have each raised portion 440 contiguously adjacent to any other raised portion 440. However, if there are a plurality of raised portions 440 collectively near the distal end of the tubular body portion as well as a plurality of raised portions 440 collectively near the proximal end of the tubular body portion, there will be two sealing regions 430 with only continuous lengths among their group. That is, the sealing region 430 in the distal end will have one continuous length of material while the sealing region 430 in the proximal end will have its own continuous length of material. The continuous length of material refers to the elastomeric material used to create the durable and flexible sealing region 430.

FIGS. 2-11 show that the raised portions 440 within the elastomeric material can have a multitude of different geometries relative to the vertical axis of the invention. For example, the raised portions 440 can have a square/rectangular (FIGS. 2-4, 6), parabolic (FIG. 11), triangular, oval, spear-like, parallelogram-like (FIG. 5), dome-like (FIG. 11), ripples (FIGS. 7 and 9), or protrusions that resemble "gripping" mechanisms or shapes that one skilled in the art would use to "grip" an object to another object. For example, a finger-like projection (FIGS. 8 and 10) that resembles a hook similar to the "hook" portion of a "hook and loop" configured as used in Velcro®. Each raised portion 440 preferably is not co-linear with the fabric exterior layer 300, as can be seen in the relevant figures.

Figure 12:
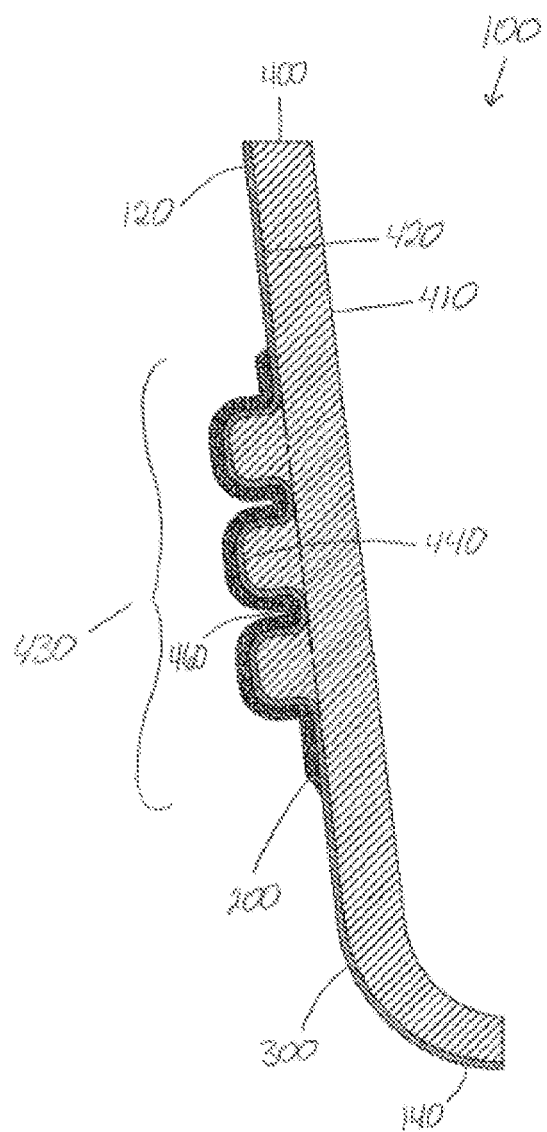
FIGS. 12-13 are cross-sectional views of suspension sleeve liners wherein alternate embodiments of the raised portions are shown.
Figure 13:
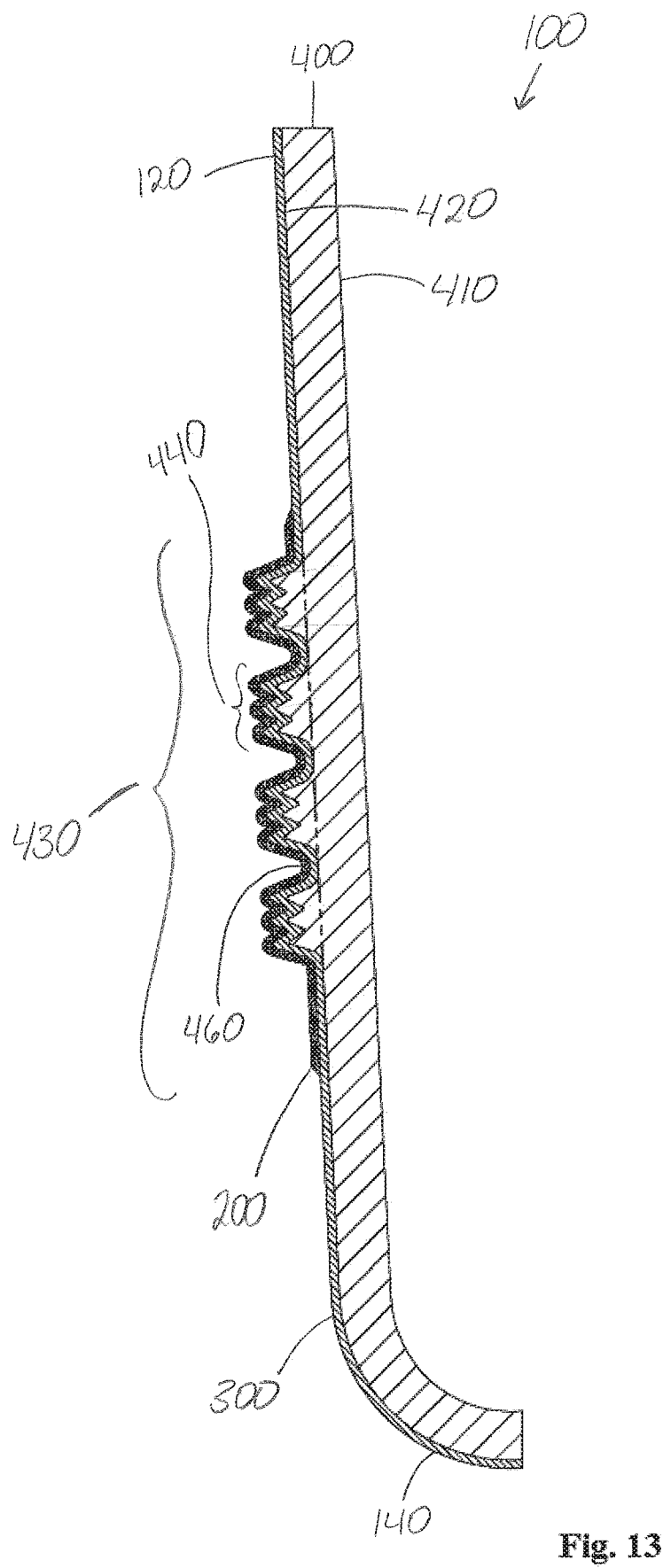

FIGS. 12 and 13 show the seal liner 100 without recessed portions 450 in the elastomeric layer 400. The raised portions 440 protrude from the elastomeric layer 400 without recessed portions 450 located between, among, or near the raised portions 440. This embodiment of the seal liner 100 is useful because of its ease of manufacturing and slimmer profile. Only the reinforcement layer 200 and fabric exterior layer 300 have recessed portions 450 which correspond to the recesses 450 between each raised portion 440.

Figure 14:
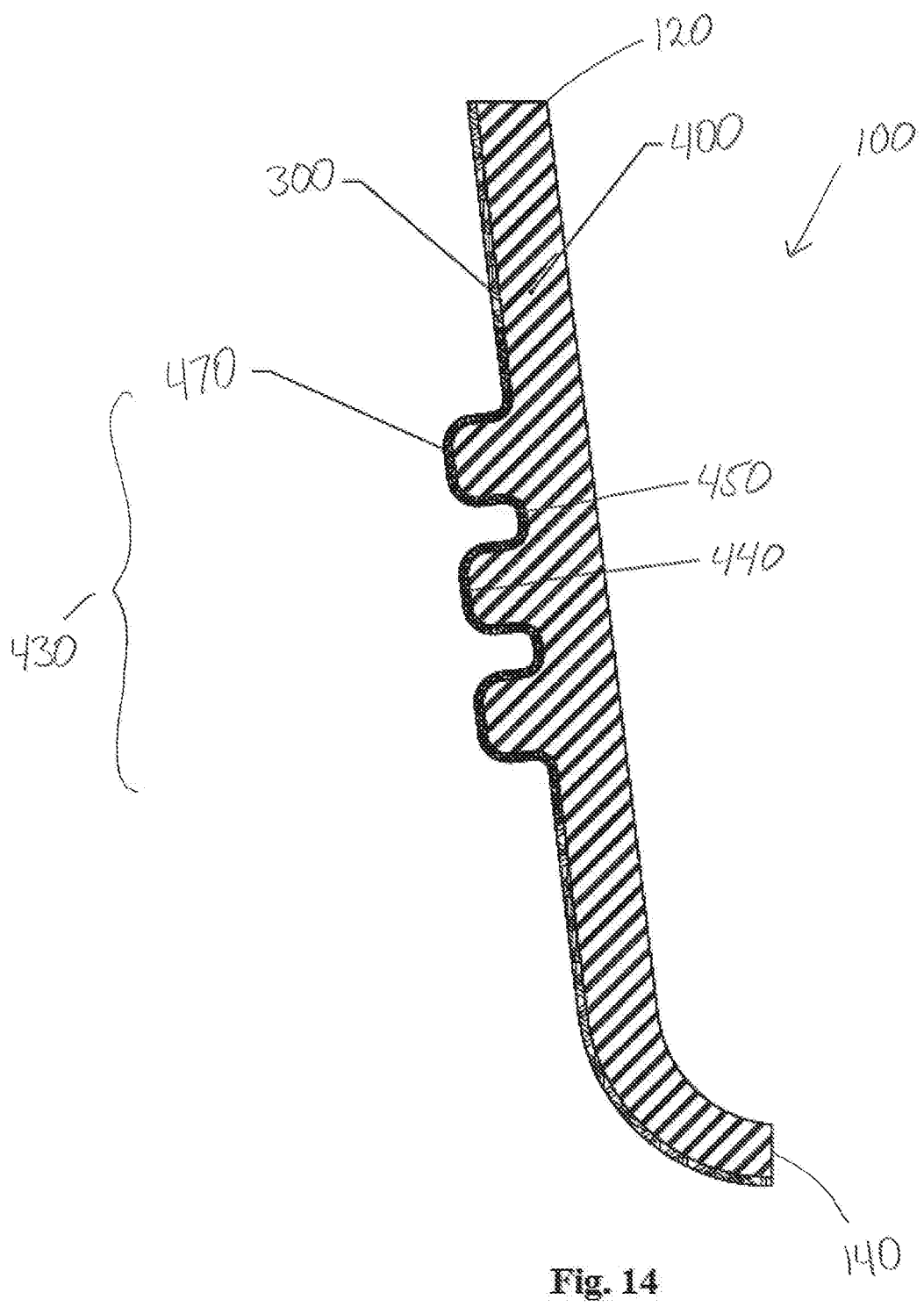
FIGS. 14-15 are cross-sectional views of suspension sleeve liners wherein alternate embodiments of the raised portions are shown, specifically liners having an elastomeric material impregnated within a fabric exterior layer.

FIG. 14 shows an additional embodiment of the seal liner 100 which includes having elastomeric material impregnated within the fabric exterior 300 along the entire length of the sealing region 430. The elastomeric material penetrates at least partially within the fabric exterior 300 and, preferably, is completely impregnated within the fabric exterior 300.

Furthermore, having the elastomeric material impregnated within the fabric exterior 300 allows the resulting composite to have more durable properties as compared to having the elastomeric material attached as its own layer apart from the fabric exterior 300 (FIGS. 2-13). That is, the fabric exterior 300 in conjunction with the impregnated elastomeric material has similar characteristics as having reinforcing bars ("rebar") positioned within concrete structures.

Figure 15:
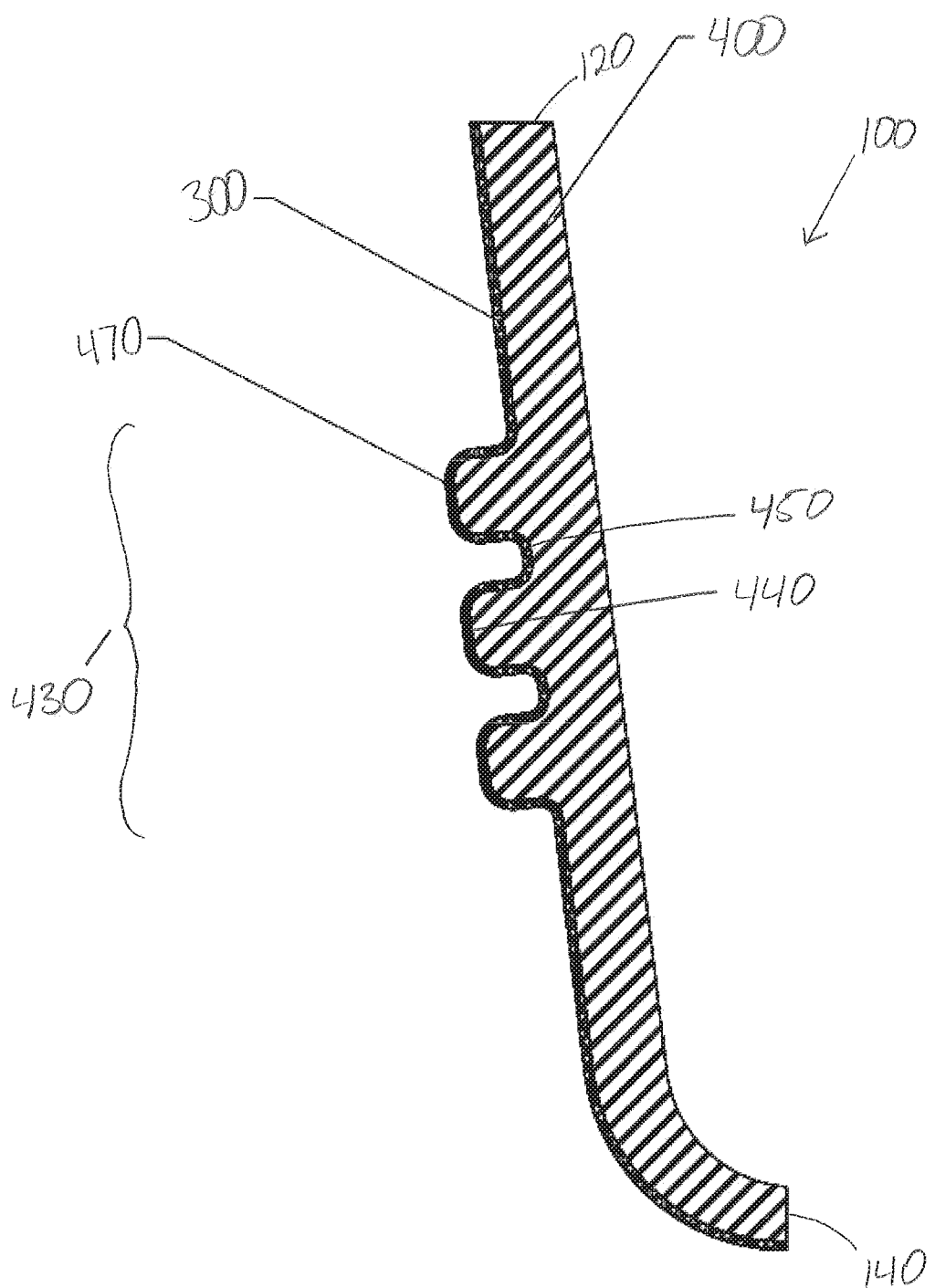

FIG. 15 shows the uses of having an apex surface 470 of the raised portions 440. The elastomeric material is fully impregnated within the fabric exterior 300 only on the apex surface 470 of the raised portions 440, as opposed to FIG. 14, which shows the elastomeric material impregnated into the fabric exterior 300 along the entire length of the sealing region 430.

Figure 8:
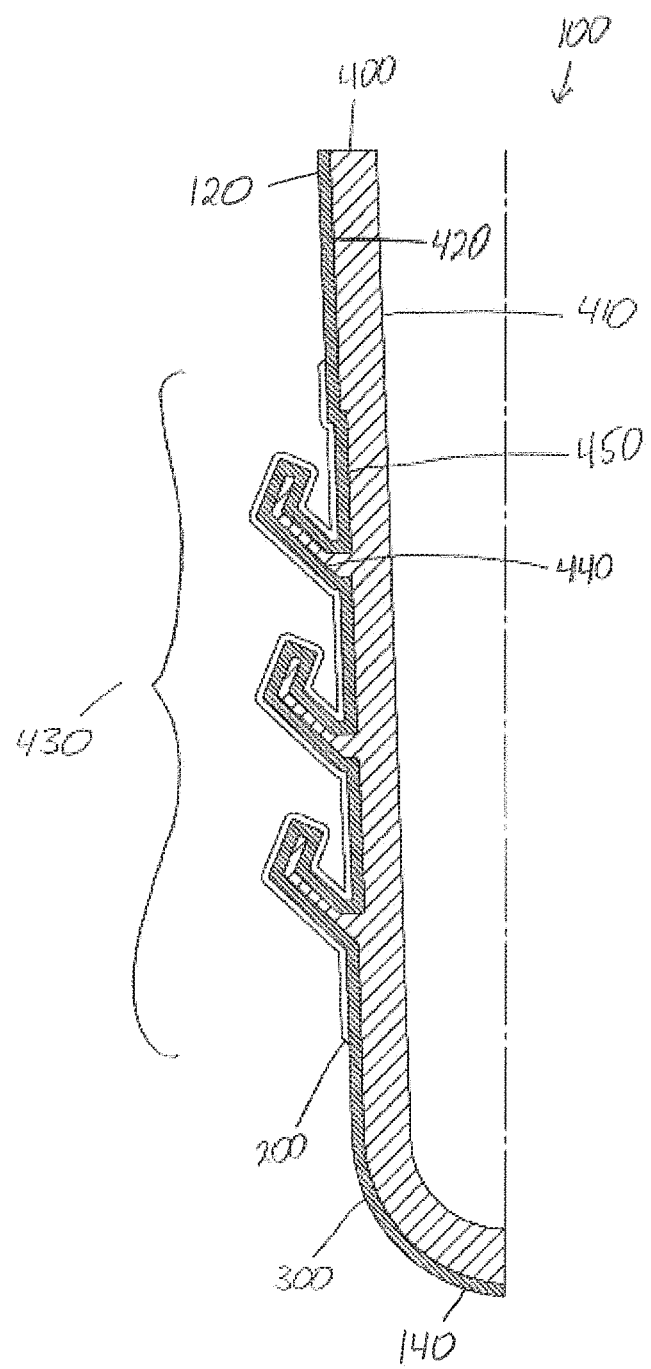
Figure 9:
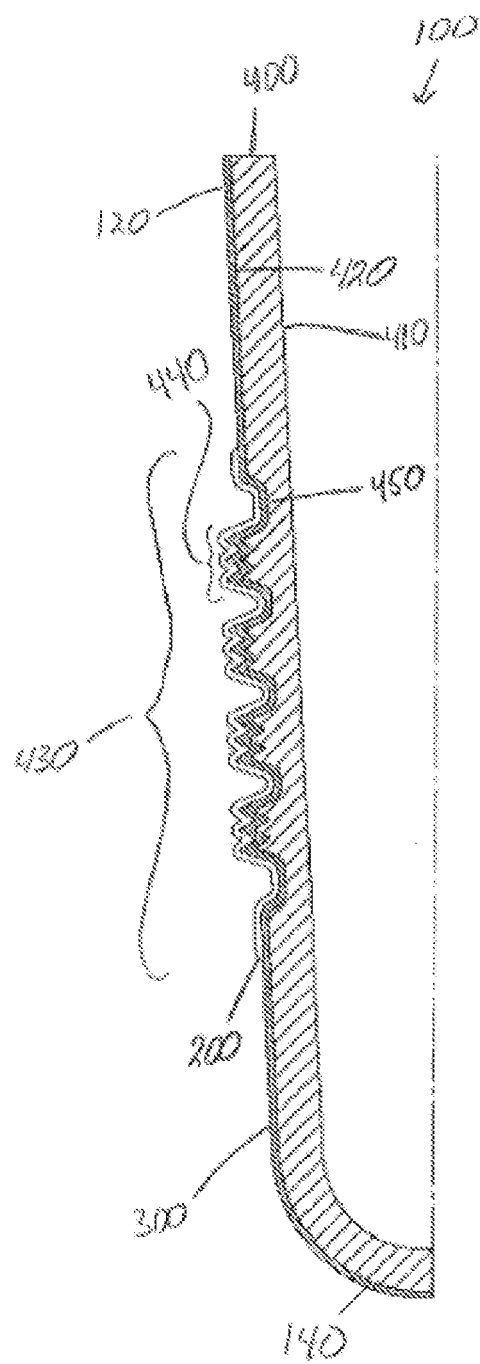
Figure 10:
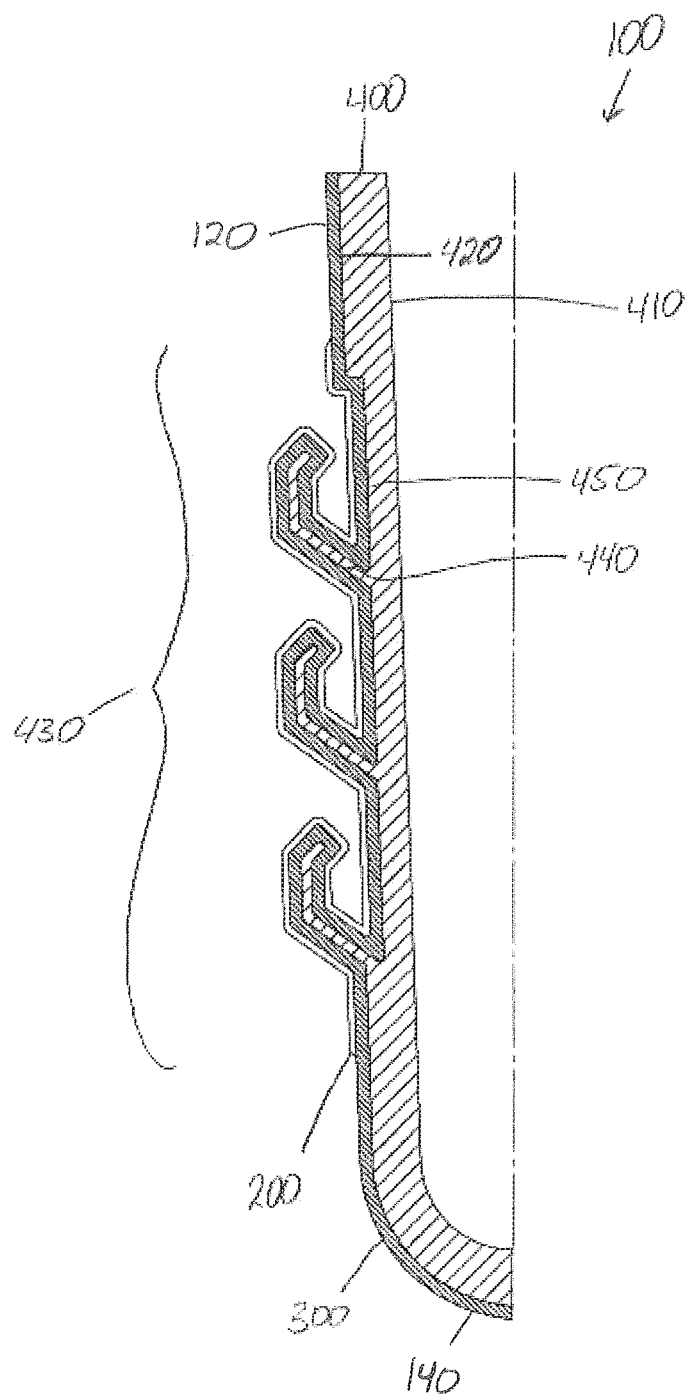
Figure 11:
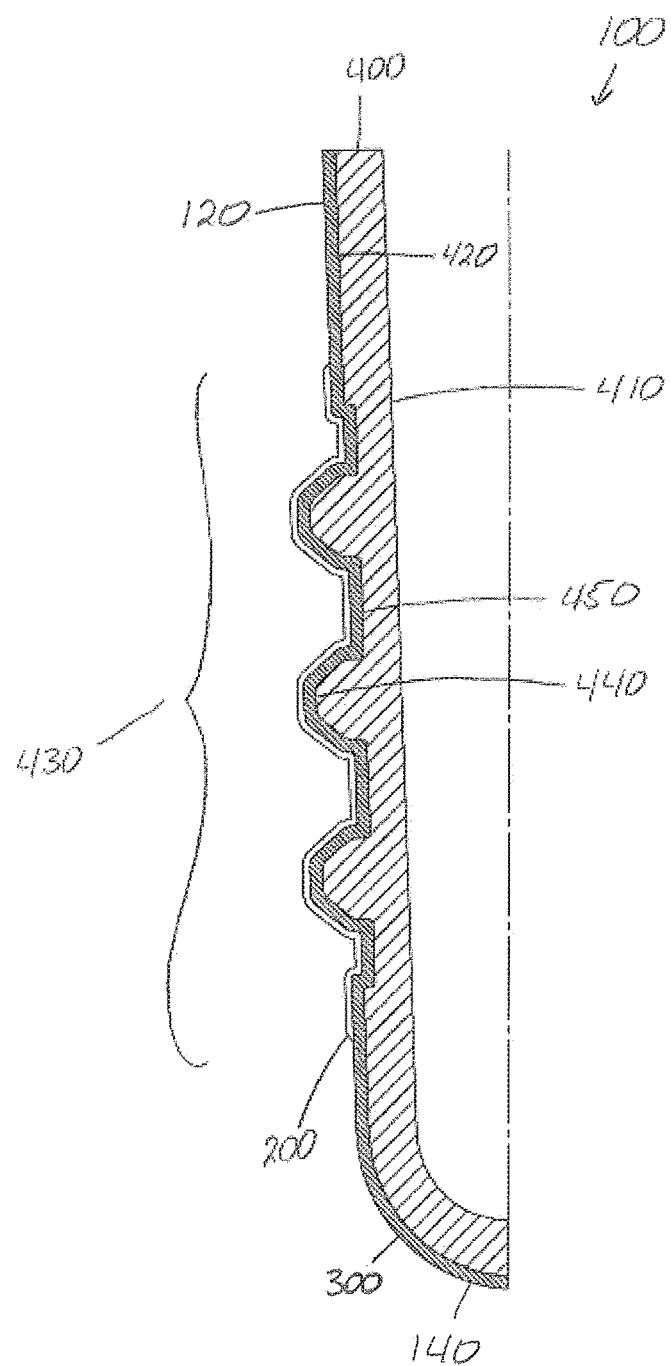

Furthermore, the apex surface 470 is just that, the highest or furthest point from the recessed portion 450. In the case of the embodiment shown in FIG. 7, for example, the apex surface 470 would be relatively at the "tip" of the triangular-like raised portion 440 and extend down towards the recessed portion 450. In FIG. 8, the apex surface 470 would be the end of the finger-like projection. The apex surface 470 may also be viewed as the surface area of the raised portion 440 that comes into contact with the socket wall.

Preparing the embodiment shown in FIGS. 14 and 15 involves four steps. First, a tube having an inflatable bladder is inserted into the seal liner 100. The inflatable bladder is positioned to be near the sealing region 430. Vinyl tape is then used to wrap the areas of the raised portions 440 to prevent any unwanted silicone from bonding to any other area apart from the apex surface of the raised portions 440. The borders created from the applied vinyl tape will define the edges of the seal area. Compressed air is then used to inflate the bladder, which will stretch the fabric exterior 300 to allow the silicone to penetrate the fabric exterior 300. The tube is then placed on a rotating arm which will rotate the seal liner 100 to allow uniform coating of the apex surface 470 of the raised portions 440, while preventing the silicone from dripping by using the principle of centrifugal force.

Second, a calibrated scale and clean mixing container are used to prepare and mix the required silicone to be applied to the apex surface 470 of the raised portions 440. Although in this method, silicone is used as the sealing material, any equivalent material may be used.

Third, the seal liner 100 is rotated while a brush or other applier is used to apply the prepared silicone to the apex surface 470 of the raised portions 440. The applied silicone is uniform and only introduced to the areas within the sealing region 430 that do not have the vinyl tape applied. No bubbles are be present within the applied silicone. The bladder is then deflated and vinyl tape removed.

Fourth, the seal liner 100 is slowly rotated on the rotating arm while an infrared heat lamp is applied approximately 1 inch from the surface of the silicone. The seal liner 100 is left to cure for approximately 10 to 20 minutes or until the silicone is no longer tacky to the touch. If the silicone coating is still liquid or soft, the seal liner 100 is left rotating to cure longer. Once the silicone is cured enough to remain in place without rotating, the seal liner 100 is moved to a clean location to finish curing overnight at room temperature.

Moreover, the impregnating process of the silicone onto the fabric exterior 300 can be accomplished in a variety of ways, including applying pre-made, semi-cured silicone strips onto the apex surface 470 of the raised portions 440. The process of applying may include painting, spraying, coating, spreading, injecting, forming, or dipping the seal liner 100 into the silicone material without inflating the seal liner 100.

Many stress and abrasion tests were successfully performed to show that the seal liner 100 would retain a vacuum while in use because of its durable sealing region 430. The seal liner 100 was first subjected to a vacuum test to establish a baseline for the level of vacuum achieved within the seal liner 100 and socket (vacuum achieved 23 inches Hg, vacuum maintained 20 inches Hg, and the duration of test was 24 hours). After the baseline was established, the elastomeric material impregnated within the fabric exterior layer 300 was gradually removed by abrasive forces to monitor the resulting vacuum level. The first sanding step removed a small layer of the elastomeric material impregnated within the fabric exterior 300 at the apex surface 470 of the raised portions 440 (vacuum achieved 22.5 inches Hg, vacuum maintained 20 inches Hg, and the duration of test was 24 hours). There was no noticeable loss of vacuum. The second sanding step removed a much thicker layer of elastomeric material impregnated with the fabric exterior 300 and again, no noticeable loss of vacuum was achieved (vacuum achieved 18.5 inches Hg, vacuum maintained 17.5 inches Hg, and the duration of test was 24 hours). The sanding steps continued until progressively, each raised portion 440 had a significant loss of impregnated elastomeric material within the fabric exterior 300 (vacuum achieved 23 inches Hg, vacuum maintained 20 inches Hg, and the duration of test was 24 hours). No noticeable loss of vacuum was achieved. Over the course of the many trials of the sanding steps, the seal liner 100 never lost more than 4.5 inches Hg and on average never lost more than 2 inches Hg.

When worn by an amputee and inserted into a socket for use with a vacuum system, the volume of air within the socket and below the seal layer is evacuated thereby securing the residual limb within the socket. The present invention thereby preferably reduces any potential for a tourniquet effect created by the vacuum process and provides high abrasion resistance.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A suspension liner sleeve configured to create a vacuum between a residual limb and a prosthetic socket comprising:
   an elongate, tubular body portion formed of a thermoplastic elastomeric material having a tubular thickness, a vertical axis, defining an open proximal region and a closed distal region, and having at least one sealing region;
   each sealing region comprising more than one raised sealing portion annularly protruding along said vertical axis and molded integrally with the tubular body portion;
   each raised sealing portion further having an apex surface;
   a fabric exterior layer bonded to said tubular body portion wherein each raised sealing portion does not extend through the fabric exterior layer; and
   an outer sealing layer comprising a cured elastomeric material impregnated within said fabric exterior layer covering each sealing region and any space between each raised sealing portion.

2. The suspension liner of claim 1 wherein said tubular body portion further comprises at least one annular recessed portion having a thickness less than said tubular thickness and positioned at a location near each raised sealing portion along said vertical axis.

3. The suspension liner of claim 1 wherein said fabric exterior layer has a uniform thickness.

4. The suspension liner of claim 1 wherein said open proximal region has a larger circumference and volume than said closed distal region.

5. The suspension liner of claim 1 wherein said tubular body portion is formed from a material selected from the group consisting of silicones, polyurethanes, block copolymers, styrene block copolymer gels, controlled distribution polymers, and crystalline polymers.

6. The suspension liner of claim 5 wherein said tubular body portion has a thickness between 2 and 9 mm.

7. The suspension liner of claim 1 wherein each raised sealing portion has a thickness between 3 and 20 mm.

8. The suspension liner of claim 1 wherein said elastomeric material of the sealing region is formed of a material selected from the group consisting of natural rubber, silicone, polyurethane, latex, polysulfide, vinyl, polyisoprene, and styrene block copolymer gel.

9. The suspension liner of claim 1 wherein said sealing region is located near the closed distal region of the tubular body.

10. The suspension liner of claim 1 wherein said sealing region layer is located near the open proximal region of the tubular body.

11. The suspension liner of claim 1 wherein said elastomeric material of the sealing region is only partially impregnated within said fabric exterior layer.

12. A suspension liner sleeve configured to create a vacuum between a residual limb and a prosthetic socket comprising:
    an elongate, tubular body portion formed of a thermoplastic elastomeric material and having an axis and defining an open proximal region and a closed distal region;
    more than one raised sealing portion annularly extending along the axis and having a distal location and a proximal location, each raised sealing portion further having a thickness wherein the thickness is greatest in between the distal location and the proximal location and molded integrally with the tubular body portion;
    said raised sealing portion further having an apex surface;
    said tubular body portion covered by a fabric exterior layer wherein said raised sealing portion does not extend through the fabric exterior layer; and
    a sealing region formed of a cured elastomeric material impregnated within said fabric exterior layer covering at least said apex surface of each raised sealing portion and any space between each raised sealing portion.

13. The suspension liner of claim 12 wherein said tubular body portion further comprises at least one annular recessed portion having a thickness less than said tubular body portion and positioned at a location near each raised sealing portion along said axis.

14. The suspension liner of claim 12 wherein said fabric exterior layer has a uniform thickness.

15. The suspension liner of claim 12 wherein said open proximal region has a larger circumference and volume than said closed distal region.

16. The suspension liner of claim 12 wherein said tubular body portion is formed from a material selected from the group consisting of silicones polyurethanes, block copolymers, styrene block copolymer gels, controlled distribution polymers, and crystalline polymers.

17. The suspension liner of claim 12 wherein said tubular body portion has a thickness of between 2 and 9 mm.

18. The suspension liner of claim 12 wherein each raised sealing portion has a thickness of between 3 and 20 mm.

19. The suspension liner of claim 12 wherein said elastomeric material of the sealing region is formed of a material selected from the group consisting of natural rubber, silicone, polyurethane, latex, polysulfide, vinyl, polyisoprene and styrene block copolymer gel.

20. The suspension liner of claim 12 wherein said sealing region is located near the closed distal region of the tubular body.

21. The suspension liner of claim 12 wherein said sealing region is located near the open proximal region of the tubular body.

22. The suspension liner of claim 12 wherein said elastomeric material of the sealing region is partially impregnated within said fabric exterior layer.

* * * * *